United States Patent [19]

Resconi et al.

[11] Patent Number: 6,107,431
[45] Date of Patent: Aug. 22, 2000

[54] REACTOR BLEND POLYPROPYLENE, PROCESS FOR THE PREPARATION THEREOF AND PROCESS FOR PREPARING METALLOCENE LIGANDS

[75] Inventors: Luigi Resconi; Fabrizio Piemontesi, both of Ferrara, Italy; Lin-Chen Yu, Hockessin, Del.

[73] Assignee: Montell Technology Company BV, Netherlands

[21] Appl. No.: 09/015,128

[22] Filed: Jan. 29, 1998

Related U.S. Application Data

[62] Division of application No. 08/574,495, Dec. 19, 1995, Pat. No. 5,747,621.

[30] Foreign Application Priority Data

Dec. 20, 1994 [IT] Italy ................................ MI94A2566
Dec. 20, 1994 [IT] Italy ................................ MI94A2567

[51] Int. Cl.[7] .................................................. C08F 10/06
[52] U.S. Cl. ..................... 526/351; 526/134; 526/153; 526/129; 526/160; 526/904; 526/943; 502/103; 502/155
[58] Field of Search .................... 526/160, 351, 526/134, 153, 129, 904, 943; 502/103

[56] References Cited

U.S. PATENT DOCUMENTS

| | | |
|---|---|---|
| 4,335,225 | 6/1982 | Collette et al. . |
| 4,971,936 | 11/1990 | Wilson et al. . |
| 5,089,573 | 2/1992 | Job . |
| 5,118,649 | 6/1992 | Job . |
| 5,118,767 | 6/1992 | Job . |
| 5,118,768 | 6/1992 | Job et al. . |
| 5,270,276 | 12/1993 | Job . |
| 5,270,410 | 12/1993 | Job . |
| 5,278,264 | 1/1994 | Spaleck . |
| 5,294,581 | 3/1994 | Job . |
| 5,329,033 | 7/1994 | Spaleck et al. . |
| 5,594,080 | 1/1997 | Waymouth et al. ..................... 526/160 |
| 5,693,836 | 12/1997 | Winter et al. ........................... 526/348 |

FOREIGN PATENT DOCUMENTS

| | | |
|---|---|---|
| 0 475 307 A1 | 3/1992 | European Pat. Off. . |
| 0 530 647 A1 | 3/1993 | European Pat. Off. . |
| 0 114 391 A1 | 8/1994 | European Pat. Off. . |
| 2 001 008 | 1/1979 | United Kingdom . |
| WO 95/25757 | 9/1995 | WIPO . |

OTHER PUBLICATIONS

J.A. Ewen, "Mechanisms of Stereochemical Control in Propylene Polymerization with Soluble 4B Metallocene/Methylalumoxane Catalysts", Journal of the American Chemical Society, vol. 106, No. 21, Oct. 17, 1984 pp. 6355–6364.

Llinas et al. "Macromolecules" 1992, 25, 1242–1253.

*Primary Examiner*—David W. Wu
*Assistant Examiner*—Ling-Siu Choi
*Attorney, Agent, or Firm*—Bryan Cave LLP

[57] ABSTRACT

Fractionable, reactor blend polypropylenes, directly obtainable from the polymerization reaction of propylene, having:

(a) content of isotactic pentads (mmmm) comprised between 25 and 85%;

(b) ratio $M_w/M_n < 5$;

containing from 10 to 70% by weight of a fraction soluble in boiling diethyl ether, said fraction having a content of isotactic pentads (mmmm) comprised between 5 and 25%, and from 30 to 90% by weight of a boiling n-heptane-insoluble fraction, soluble in xylene at 135° C., said fraction having a content of isotactic pentads (mmmm) comprised between 50 and 99%, are disclosed. These polymers are suitable as thermoplastic-elastomeric materials. A process for the preparation of these polymers and a process for the preparation of 2-aryl-substituted indenyl metallocene ligands is also disclosed.

7 Claims, No Drawings

REACTOR BLEND POLYPROPYLENE, PROCESS FOR THE PREPARATION THEREOF AND PROCESS FOR PREPARING METALLOCENE LIGANDS

This application is a divisional of U.S. Patent application Ser. No. 08/574,495 filed Dec. 19, 1995 now U.S. Pat. No. 5,747,621.

BACKGROUND OF THE INVENTION

1. Field of the Invention

The present invention relates to a reactor blend polypropylene suitable as a thermoplastic-elastomeric material and to a process for the preparation thereof. It also relates to a process for the preparation of indenyl metallocene ligands.

2. Description of the Prior Art

As it is well known, the polymers of propylene can be either crystalline or amorphous. Whereas the polypropylene having isotactic or syndiotactic structure is crystalline, the polypropylene having essentially atactic structure appears to be amorphous. The atactic polypropylene, represented by the Fischer formula as described in "M. Farina, Topics Stereochem., 17, (1987), 1–111" shows methyl groups casually arranged on each side of the polymeric chain. As described in the above mentioned publication, useful information on the structure can be obtained from the N.M.R. analysis.

While crystalline polypropylenes are widely used in the manufacture of plastic products, the amorphous polypropylene available on the market, which is generally a by-product of the isotactic polypropylene obtained with Ziegler-Natta type catalysts, is mainly used in adhesive compositions and as additives for bitumens.

Polymers of propylene are further known having low crystallinity degree and showing elastomeric characteristics.

U.S. Pat. No. 4,335,225 discloses a fractionable, elastic polypropylene, having an isotactic content of 55% or less, which contain a diethyl ether-soluble fraction with an isotactic crystalline content of about 0.5–5% by weight. This polypropylene is prepared with a catalyst based on tetraalkyl zirconium supported on a metal oxide.

U.S. Pat. No. 4,971,936, U.S. Pat. No. 5,089,573, U.S. Pat. No. 5,118,649, U.S. Pat. No. 5,118,767, U.S. Pat. No. 5,118,768 and U.S. Pat. No. 5,294,581 disclose elastomeric, primarily isotactic polymers of propylene, having a narrow distribution of relatively short block lenghts.

U.S. Pat. No. 5,270,276 and U.S. Pat. No. 5,270,410 disclose elastomeric, primarily syndiotactic polymers of propylene, having a narrow distribution of relatively short block lenghts.

However, all the above elastomeric polypropylenes, due to the fact that the catalyst systems which are used for their preparation have different catalytic sites, are endowed with a wide distribution of molecular weights which reflects negatively on their properties.

More recently, catalysts based on metallocene and alumoxane compounds have been used in the polymerization reaction of olefins. Operating in the presence of these catalysts, polymers characterised by a narrow molecular weight distribution and having structural characteristics of interest have been obtained.

By polymerizing propylene in the presence of metallocene catalysts, amorphous or highly crystalline polypropylenes can be obtained depending on the metallocene used.

In particular, chiral, bridged metallocene compounds give rise to stereospecific catalysts able to polymerize propylene to highly crystalline polymers. European patent application EP 185,918, for instance, discloses a process for the preparation of isotactic polypropylene in the presence of the ethylenebis(4,5,6,7-tetrahydroindenyl)zirconium dichloride/alumoxane catalyst system.

Polymers of propylene are further known, obtainable in the presence of particular bridged metallocene catalysts, which have isotactic and atactic blocks within a single polymer chain and exhibits elastomeric properties. Polymers of this type are described by Llinas et al. in "Macromolecules, 1992, 25, 1242–1253". The polymerization is carried out in liquid toluene. The characteristics of the obtained polymers depend on the temperature of polymerization: the polymers obtained at 25–50° C. are completely soluble in diethyl ether and shows a very low melting point of about 70° C., while the polymers obtained at $\leq 0°$ C. have diethyl ether insoluble fractions but exhibit no melting endotherm. Despite the homogeneity in molecular weight distribution, the molecular weights of these polymers are not high enough and their poor crystallinity makes them unsuitable for certain applications, such as for compatibilizing blends of amorphous and crystalline polyolefins.

The problem which the present invention sets out to solve is, therefore, to provide partially crystalline thermoplastic-elastomeric propylene polymers, directly obtainable from the polymerization reaction of propylene without the need of separation steps or of sequential polymerization, which are endowed with good mechanical properties and can be suitably used as an elastomeric material and as a compatibilizer for blend s of amorphous and crystalline polyolefins.

SUMMARY OF THE INVENTION

This problem is solved according to the invention by carrying out the polymerization reaction of propylene in bulk monomer in the presence of a catalyst system based on particular unbridged 2-aryl-substituted bis-indenyl metallocenes, thus obtaining polypropylenes having narrow molecular weight distributions coupled to broad tacticity distributions.

Thus, according to a first object, the present invention provides a partially crystalline, fractionable propylene polymer, directly obtainable from the polymerization reaction of propylene.

According to another object, the present invention provides a process for the preparation of the propylene polymers of the invention.

According to a further object, the present invention provides a particularly advantageous process for the preparation of 2-aryl-indenyl ligands with high yields.

DESCRIPTION OF THE PREFERRED EMBODIMENTS

The fractionable propylene polymers of the invention have the following characteristics:

(a) content of isotactic pentads (mmmm) comprised between 25 and 85%;

(b) ratio $M_w/M_n < 5$;

said polymers contain from 10 to 70% by weight of a fraction soluble in boiling diethyl ether, said fraction having a content of isotactic pentads (mmmm) comprised between 5 and 25%, and from 30 to 90% by weight of a boiling n-heptane-insoluble fraction, soluble in xylene at 135° C., said fraction having a content of isotactic pentads (mmmm) comprised between 50 and 99%.

The propylene polymers according to the invention are actually a reactor blend polypropylene having a very broad composition distribution with regard to tacticity. In fact, they can be sequentially fractionated by solvent extraction into different fractions having gradually increasing crystallinity content, starting from substantially amorphous fractions up to fractions having a relatively high crystallinity content.

It is thus possible to isolate a fraction soluble in boiling diethyl ether representing about 10 to 90%, preferably 15 to 50%, by weight of the whole polymer, which fraction is constituted by substantially amorphous polypropylene having a content of isotactic pentads (mmmm) comprised between 5 and 25%, preferably between 10 and 25%.

Another fraction which can be isolated is a boiling n-heptane-insoluble fraction, soluble in xylene at 135° C., representing about 10 to 90%, preferably 20 to 60%, by weight of the whole polymer, which fraction is constituted by fairly isotactic chains having a content of isotactic pentads (mmmm) comprised between 50 and 99%, preferably between 60 and 85%.

In addition to the amorphous fraction extractable in diethyl ether and the most crystalline fraction insoluble in n-heptane, the polymers of the invention may contain other fractions having intermediate crystallinities. These fractions may be fractionated by extraction with solvents such as pentane, hexane, heptane.

According to one embodiment, it may thus be possible to isolate a further fraction which is insoluble in boiling diethyl ether and extractable in boiling n-heptane, constituted by chains having a content of isotactic pentads (mmmm) comprised between 25 and 60%, preferably between 30 and 50%. Said fraction may represent up to about 60% by weight of the whole polymer.

Each fraction may be further separated into sub-fractions of different crystallinity through extraction with solvents having intermediate solubilities.

Measurements of Differential Scanning Calorimetry (DSC) give information on the crystallinity of the polymers of the invention as well as of their fractions.

The melting point of the polymers of the invention depends on the degree of crystallinity. The main melting point is generally comprised between 130 and 160° C., preferably comprised between 135 and 155° C., more preferably comprised between 140 and 150° C. The enthalpy of fusion ($\Delta H_f$) of the whole polymers according to the invention is generally higher than 5 J/g, preferably higher than 10 J/g.

The diethyl ether-soluble fraction of the polymers of the invention is substantially devoid of crystallinity. Evidence to this fact is provided by the DSC measurements carried out on said fractions: no noticeable peak attributable to the enthalpy of fusion are showed.

The n-heptane-insoluble fraction of the polymers of the invention shows a melting point generally comprised between 135° C. and 155° C., preferably between 140° C. and 150° C. The enthalpy of fusion of this fraction is generally higher than 10 J/g, preferably higher than 20 J/g.

The molecular weights of the polymers of the invention are relatively high. In fact, the polymers of the invention have intrinsic viscosity values generally higher than 0.5 dl/g which, as the reaction temperature decrease, can reach values higher than 1.0 dl/g or even higher than 1.5 dl/g.

The molecular weights of the polymers of the invention, besides being high, have a relatively narrow distribution. An index of molecular weight distribution is represented by the ratio $M_w/M_n$ which, for the polymers of the invention, is lower than 5, preferably lower than 4, more preferably lower than 3.

$^{13}$C-N.M.R. analysis carried out on the polypropylene of the invention gives information on the tacticity of the polymeric chains, that is on the distribution of the configurations of the tertiary carbon atoms.

The polymers of the invention show a partially isotactic structure. In fact, it is observed that the isotactic diads (m), even if not being present in large excess, appear to be more numerous than the syndiotactic diads (r). The difference between the percent of isotactic diads (m) and the percent of syndiotactic diads (r) is generally comprised between 20 and 70, preferably between 25 and 60, more preferably between 30 and 50.

The Bernoullianity index (B), defined as:

$$B=4[mm][rr]/[mr]^2$$

has values far from the unit, generally higher than 1.5.

The structure of the polypropylene according to the invention appears to be very regioregular. In fact, from the $^{13}$C-N.M.R. analysis, signals relating to sequences $(CH_2)_n$ wherein $n \geq 2$ are not detectable. It can thus be reasonably maintained that less than 2% and, preferably, less than 1% of the $CH_2$ groups are contained in sequences $(CH_2)_n$ wherein $n \geq 2$.

The propylene polymers according to the invention can include small amounts, that is up to about 10% by mole, of comonomeric units derived from α-olefins different from propylene. Examples of these α-olefine are ethylene, 1-butene, 1-pentene, 1-hexene.

The propylene polymers according to the present invention are endowed with interesting elastomeric properties. They can be used in a variety of applications typical of amorphous or partially crystalline elastomeric polypropylenes. The polymers of the invention, due to their peculiar characteristics, find a particularly interesting utilization as compatibilizers for blends of crystalline and amorphous polyolefins, such as isotactic and atactic polypropylenes. Example of possible applications include car bumpers, medical contacts, grafting stocks and the like.

The present invention also provides a process for the preparation of the propylene polymers according to the invention, said process comprising the polymerization reaction of propylene, in a polymerization medium consisting essentially of liquid propylene, in the presence of a catalyst comprising the product of the reaction between:

(A) a metallocene compound of formula (I)

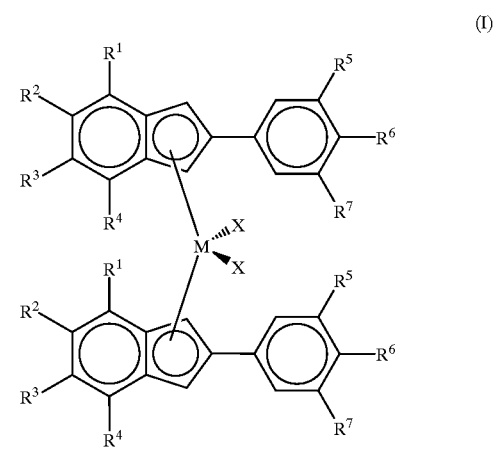

wherein on each indenyl group the $R^1$, $R^2$, $R^3$, $R^4$, $R^5$, $R^6$ and $R^7$ substituents, same or different from each other, are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkylaryl radicals, or $C_7$–$C_{20}$ arylalkyl radicals, optionally two adjacent $R^1$, $R^2$, $R^3$, $R^4$, $R^5$, $R^6$ and $R^7$ substituents on the same ring can form a cycle comprising from 5 to 8 carbon atoms and, furthermore, substituents $R^1$ can contain Si or Ge atoms;

M is a transition metal of group IVb, Vb or VIb of the Periodic Table of The Elements;

substituents X, the same or different from each other, are hydrogen atoms, halogen atoms, —$R^8$, —$OR^8$, —$SR^8$, —$NR^8_2$ or —$PR^8_2$ groups, wherein substituents $R^8$ are $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkylaryl radicals, or $C_7$–$C_{20}$ arylalkyl radicals, and can contain Si or Ge atoms; and (B) an alumoxane, or one or more compounds able to give a metallocene alkyl cation.

Though not pretending to be bound by theory, it is believed that in the process of the invention two different active species (rotamers) of the metallocene, one chiral and the other achiral, are in equilibrium of isomerization during chain growth and that, in the condition of the process of the invention, the rate of isomerization is of the same order of magnitude of the rate of growth of a single polymer chain.

The polymerization temperature is generally comprised between −50° C. and +80° C., preferably between 0° C. and +50° C. According to a particularly preferred embodiment, the polymerization temperature is comprised between 20° C. and 40° C.

The content of isotacticity of the polymers of the invention is function of the polymerization temperature, with a maximum around 20–30° C.

The polymerization temperature has also an influence on the molecular weight of the polymers of the invention. The lower the polymerization temperature, the higher the molecular weight of the polymers obtained.

The molecular weight of the polymers may be additionally varied by altering the concentration of the catalytic components or using molecular weight regulators such as, for example, hydrogen.

The molecular weight distribution may be varied by using mixtures of different metallocene compounds, or carrying out the polymerization in several stages that differ in polymerization temperature and/or concentration of molecular weight regulator.

Among the metallocene compounds of formula (I) are preferred those in which, in each of the indenylic ligand, the substituents $R^1$ are the same as substituents $R^4$, and the substituents $R^2$ are the same as substituents $R^3$. More preferably the substituents $R^1$ and $R^4$ are hydrogen atoms and, even more preferably, all the substituents $R^1$, $R^2$, $R^3$ and $R^4$ are hydrogen atoms.

In the metallocene compounds of formula (I) the transition metal M is preferably selected among titanium, zirconium and hafnium, more preferably is zirconium.

In the metallocene compounds of formula (I) the substituents X are preferably chlorine atoms or methyl radicals.

Non limiting examples of metallocene compounds for use in the process of the invention are:

bis(2-phenyl-indenyl)zirconium dichloride,
bis[2-(4-methylindenyl)-indenyl]zirconium dichloride,
bis[2-(4-t-butyl-phenyl)-indenyl]zirconium dichloride,
bis[2-(4-phenyl-phenyl)-indenyl]zirconium dichloride,
bis[2-(4-fluoro-phenyl)-indenyl]zirconium dichloride,
bis[2-(4-trifluoromethyl-phenyl)-indenyl]zirconium dichloride,
bis[2-(3,5-dimethyl-phenyl)-indenyl]zirconium dichloride,
bis[2-(3,5-bis-trifluoromethyl-phenyl)-indenyl]zirconium dichloride,
bis(2-phenyl-4,7-dimethyl-indenyl)zirconium dichloride,
bis(2-phenyl-4,6-dimethyl-indenyl)zirconium dichloride,
bis(2-phenyl-5,6-dimethyl-indenyl)zirconium dichloride,
bis(2-phenyl-4,5,6,7-tetramethyl-indenyl)zirconium dichloride,
bis(2-phenyl-indenyl)zirconium dimethyl,
bis(2-phenyl-4,7-dimethyl-indenyl)zirconium dimethyl,
bis(2-phenyl-4,6-dimethyl-indenyl)zirconium dimethyl,
bis(2-phenyl-5,6-dimethyl-indenyl)zirconium dimethyl,
bis(2-phenyl-4,5,6,7-tetramethyl-indenyl)zirconium dimethyl.

In the catalysts for use in the process of the invention, both the metallocene compound of formula (I) and the alumoxane can be present as product of reaction with a organometallic compound of aluminium of formula $AlR^9_3$ or $Al_2R^9_6$, in which substituents $R^9$, same or different from each other, are defined as the substituent $R^8$ above or are halogen atoms.

Non limitative examples of aluminium compounds of formula $AlR_3$ or $Al_2R^4_6$ are:
$Al(Me)_3$, $Al(Et)_3$, $AlH(Et)_2$, $Al(iBu)_3$, $AlH(iBu)_2$, $Al(iHex)_3$, $Al(C_6H_5)_3$, $Al(CH_2C_6H_5)_3$, $Al(Ch_2CMe_3)_3$, $Al(CH_2SiMe_3)_3$, $Al(Me)_2iBu$, $Al(Me)_2Et$, $AlMe(Et)_2$, $AlMe(iBu)_2$, $Al(Me)_2iBu$, $Al(Me)_2Cl$, $Al(Et)_2Cl$, $AlEtCl_2$, $Al_2(Et)_3Cl_3$, wherein Me=methyl, Et=ethyl, iBu=isobutyl, iHex=isohexyl.

Among the above mentioned aluminium compounds, trimethylaluminium (TMA) and triisobutylaluminium (TIBAL) are preferred.

The alumoxane used in the catalyst according to the invention is a linear, branched or cyclic compound, containing at least one group of the type:

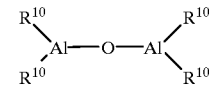

where the substituents $R^{10}$, same or different from each other, are defined as substituents $R^8$ or are a —O—$Al(R^{10})_2$ group, and optionally some of the $R^{10}$ groups can be halogen atoms.

In particular, it is possible to use alumoxanes of formula:

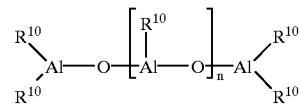

in the case of linear compounds, wherein n is 0 or an integer comprised between 1 and 40, and the substituents $R^{10}$, same or different from each other, are defined as substituents $R^8$, or alumoxanes of formula:

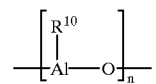

in the case of cyclic compounds, wherein n is an integer comprised between 2 and 40, and the substituents $R^{10}$, same or different from each other, are defined as substituents $R^8$.

Substituents $R^{10}$ are preferably methyl, ethyl or isobutyl groups.

Examples of alumoxanes suitable for the use according to the present invention are methylalumoxane (MAO) and tetraisobutyl-dialumoxane (TIBAO).

Non limitative examples of compounds able to form a metallocene alkyl cation are compounds of formula $Y^+Z^-$, wherein in $Y^+$ is a Bronsted acid, able to give a proton and to react irreversibly with a substituent $R^2$ of the compound of formula (I) and $Z^-$ is a compatible anion, which does not coordinate, which is able to stabilize the active catalytic species which originates from the reaction of the two compounds and which is sufficiently labile to be able to be removed from an olefinic substrate. Preferably, the anion $Z^-$ comprises one or more boron atoms. More preferably, the anion $Z^-$ is an anion of the formula $BAr^{(-)}_4$, wherein substituents Ar, the same or different from each other, are aryl radicals such as phenyl, pentafluorophenyl, bis (trifluoromethyl)phenyl. Particularly preferred is the tetrakis-pentafluorophenyl borate. Furthermore, compounds of formula $BAr_3$ can be suitably used.

The catalysts of the present invention can also be used on an inert support. That is by depositing the metallocene compound (A), or the reaction product of the metallocene (A) with component (B), or the component (B) and successively the metallocene compound (A), on the inert support such as for example, silica, alumina, styrene-divinylbenzene copolymers or polyethylene. The solid compound so obtained can be used in combination with further addition of the alkyl aluminium compound as such or prereacted with water, if necessary.

The polymerization yield depends on the purity of the metallocenic component on the catalyst. Moreover, the metallocene compounds obtained by the process of the invention may be used as such, or undergo purification treatment.

The catalyst components may be brought into contact before polymerization. The contact time is generally comprised between 1 and 60 minutes, preferably between 5 and 20 minutes. The precontact concentrations for the metallocene compound (A) are comprised between $10^{-2}$ and $10^{-8}$ mol/l, whilst for the component (B) are comprised between 10 and $10^{-3}$ mol/l. The precontact is generally carried out in the presence of a hydrocarbon solvent and, optionally, small amounts of monomer.

The metallocene compounds of formula (I) may be prepared through reaction of the corresponding indenyl ligands substituted in 2-position of formula (II):

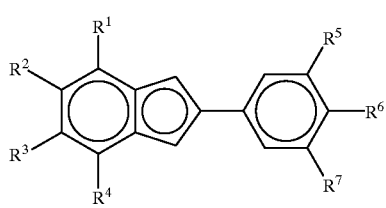

(II)

where $R^1$, $R^2$, $R^3$, $R^4$, $R^5$, $R^6$ and $R^7$ have the meaning described above, firstly with a compound capable of forming an delocalised anion on the cyclopentadienyl ring, and subsequently with a compound of formula $MX_4$, where M and substituents X have the above defined meaning.

In the case in which at least one substituent X in the metallocene compound of formula (I) to be prepared is different from halogen, it is necessary to substitute at least one substituent X in the metallocene obtained with at least one substituent X different from halogen.

The substitution reaction of substituent X with substituent X different from halogen is carried out through generally used methods. For example, when the substituents X desired are alkyl groups, the metallocenes may be made to react either with a alkylmagnesium halide (Grignard reaction) or with alkyl lithium compounds.

The invention further provides a particularly advantageous process for the preparation of the indenyl ligands of formula (II) with high yields, said process comprising:

(a) the reaction of a $4\text{-}R^1\text{-}5\text{-}R^2\text{-}6\text{-}R^3\text{-}7\text{-}R^4$-indan-2-one with a compound of formula $(3\text{-}R^5\text{-}4\text{-}R^6\text{-}5\text{-}R^7$-phenyl)$YZ_m$, wherein $R^1$, $R^2$, $R^3$, $R^4$, $R^5$, $R^6$ and $R^7$ have the above defined meaning, Y is a metal is selected from alkaline and earth-alkaline metals, Z is an halogen atom, m is 0 when Y is an alkaline metal and is 1 when Y is an earth-alkaline metal;

(b) the subsequent treatment with an acid medium, to obtain the corresponding $2\text{-}(3\text{-}R^5\text{-}4\text{-}R^6\text{-}5\text{-}R^7$-phenyl)$\text{-}4\text{-}R^1\text{-}5\text{-}R^2\text{-}6\text{-}R^3\text{-}7\text{-}R^4$-indan-2-ol; and (c) the dehydration reaction of the $2\text{-}(3\text{-}R^5\text{-}4\text{-}R^6\text{-}5\text{-}R^7$-phenyl)$\text{-}4\text{-}R^1\text{-}5\text{-}R^2\text{-}6\text{-}R^3\text{-}7\text{-}R^4$-indan-2-ol;

characterized in that the reaction of the $4\text{-}R^1\text{-}5\text{-}R^2\text{-}6\text{-}R^3\text{-}7\text{-}R^4$-indan-2-one with the compound of formula $(3\text{-}R^5\text{-}4\text{-}R^6\text{-}5\text{-}R^7$-phenyl)$YZ_m$ is carried out in the presence of a compound of a metal selected from lanthanum and the lanthanides.

Preferred organometallic halides of formula $(3\text{-}R^5\text{-}4\text{-}R^6\text{-}5\text{-}R^7$-phenyl)$YZ_m$ are the aryl magnesium halides and, particularly preferred, the aryl magnesium bromides.

The reaction between the indan-2-one and the compound of formula $(3\text{-}R^5\text{-}4\text{-}R^6\text{-}5\text{-}R^7$-phenyl)$YZ_m$ is preferably carried out in the presence of an halide, more preferably chloride, of a metal of the lanthanide series. A particularly suitable compound for use in the above reaction is cerium chloride.

The reaction between the indan-2-one and the compound of formula $(3\text{-}R^5\text{-}4\text{-}R^6\text{-}5\text{-}R^7$-phenyl)$YZ_m$ is generally carried out at a temperature comprised between −100 and 40° C., and it is generally carried out in the presence of one ore more solvents such as, for example, tetrahydrofuran, diethyl ether, cyclohexane or pentane.

The compound of a metal selected from lanthanum and the lanthanides used in step (a) of the process for preparing the ligands of formula (II) is generally used in quantities comprised between 0.5 and 10 equivalents. A particularly suitable amount is of about 1.5 equivalents.

Non limitative examples of acids mediums for use in the treatment of step (b) are, hydrochloric acid, sulphuric acid, p-toluene-sulphonic acid, potassium bisulphate.

The 2-aryl-indan-2-oles may be conveniently separated from the reaction mixture obtained at step (b) by extraction with solvents such as, for example, diethyl ether, pentane, cyclohexane, benzene or toluene and subsequent distillation.

The dehydration reaction of step (c) is generally carried out in the presence of an acid such as, for example, hydrochloric acid, sulphuric acid, p-toluene-sulphonic acid, potassium bisulphate.

The 2-aryl-indenes of formula (II) may be conveniently separated from the reaction mixture obtained from step (c) by extraction with solvents such as, for example, diethyl ether, pentane, cyclohexane, benzene or toluene and subsequent distillation.

Further advantages of the present invention are made clear by the following examples, which are given to illustrate and not to limit the invention.

CHARACTERISATIONS

The intrinsic viscosity [η] has been measured in tetrahydronaphtalene at 135° C.

The molecular weight distribution has been determined by GPC using a WATERS 150 instrument in orthodichlorobenzene at 135° C.

The Differential Scanning Calorimetry (DSC) measurements have been carried out on a DSC-7 apparatus of Perkin Elmer Co. Ltd., according to the following procedure. About 10 mg of sample are heated to 180° C. with a scanning speed equal to 10° C./minute; the sample is kept at 180° C. for 5 minutes and thereafter is cooled with a scanning speed equal to 10° C./minute. A second scanning is then carried out according to the same modalities as the first one. Values reported are those obtained in the second scanning.

The $^{13}$C-N.M.R. analysis of the polymers were carried out by a Bruker AC200 instrument at 50,323 MHz, using $C_2D_2Cl_4$ as solvent (about 300 mg of polymer dissolved in 2.5 ml of solvent), at 120° C.

PREPARATION OF THE METALLOCENES

All the operations have been carried out under an inert atmosphere.

THF=tetrahydrofuran
Et$_2$O=diethyl ether

EXAMPLE 1

BIS(2-PHENYL-INDENYL)ZIRCONIUM DICHLORIDE (a) Preparation of 2-phenyl-indan-2-ol A suspension of anhydrous cerium chloride (40.60 g, 164.7 mmol) in THF (270 mL) was stirred at room temperature for 2 hours under nitrogen. Phenylmagnesium bromide (46.5 mL of 3.0 M solution in diethyl ether, 139.5 mmol) was added at 0° C. and stirred for 3.5 h. A solution of 2-indanone (14.21 g, 107.7 mmol) in THF (20 mL) was added at the same temperature. After stirring at 0° C. for 3 hours, the mixture was allowed to warm to room temperature and kept at ambient temperature for 12 h. It was then treated with 5% aqueous hydrochloric solution. The solution was extracted with diethyl ether (4*200 mL). All etheral layers were combined, washed with water (100 mL), dried over anhydrous magnesium sulphate and concentrated to give the crude product. Kugelrohr distillation (150° C./0.25 mm Hg yielded 18.58 g (82%) of 2-phenyl-2-indanol in solid form (mp 54° C.). $^1$H-N.M.R. (CDCl$_3$) d 2.24 (br s, 1H), d 3.20 (d, J=16.2 Hz, 2H), d 3.43 (d, J=16.2 Hz, 2H), d 7.18–7.40 (m, 7H), d 7.51(br d, J=7.1 Hz, 2H)

(b) Preparation of 2-phenyl-1H-indene

To a solution of 2-phenyl-2-hydroxy-2,3-dihydro-1H-indene (6.88 g, 32.76 mmol) in THF (200 mL) was added a solution of concentrated hydrochloric acid (40 mL) in water (60 mL). The solution was stirred at room temperature for 3 day. Diethyl ether (200 mL) and water added. Aqueous layer was extracted with diethyl ether (3*200 mL). All etheral layers were combined, washed with water (50 mL), brine (50 mL), dried over anhydrous magnesium sulphate, and concentrated to yield 5.60 g (92%) of 2-phenyl-1H-indene. $^1$H-N.M.R. (CDCl$_3$) d 3.78 (t, J=0.8 Hz, 2H), d 7.18–7.48 (m, 8H), d 7.63(br d, J=7.1 Hz, 2H).

(c) Preparation of bis(2-phenyl-indenyl)zirconium dichloride 4.0 g of 2-phenyl-indene obtained at point (b) were dissolved in 30 ml of THF. This solution was added dropwise to a solution of 0.93 g of KH in THF. On completion, the solution was maintained under stirring at room temperature for 2 hours. The access KH was removed by decantation and the brown coloured solution was added dropwise to a solution containing 3.93 g of ZrCl$_4$(THF)$_2$ in 50 ml of Et$_2$. On completion, the brownish yellow suspension is kept under stirring for a further 2 hours, then concentrated under vacuo until a volume of about 5 ml is reached. An equal volume of Et$_2$O is then added, kept under stirring for a few minutes, then filtered and the solid portion is separated through a Sohxlet apparatus with CH$_2$Cl$_2$. The product is partially precipitated during the separation. After having removed the CH$_2$Cl$_2$ under vacuo, 4.56 g of yellow solid were obtained, containing about 8% by moles of the starting ligand. This product was further purified by washing with Et$_2$O (2×10 ml). The remaining yellow coloured solid was dried under vacuo, thus obtaining 3.97 g of yellow bis(2-phenyl-indenyl)zirconium dichloride, still containing traces of non-reacted ligand. Yield 69%. 0.5 g of this product was further purified by crystallization from toluene at −20° C., thus obtaining a pure product. $^1$H-N.M.R. (δ, ppm, CDCl$_3$): 7.57–7.40 (m, 10H), 7.16–7.20 (m, 8H), 6.63 (bs, 4H).

EXAMPLE 2 (comparison)

Phenylmagnesium chloride (75 mL of 2.0 M solution in diethyl ether, 150 mmol) was added to a solution of 2-indanone (14.94 g, 107.7 mmol) in THF (100 mL) at the same temperature. The mixture was stirred at ambient temperature overnight (12 hours). It was then treated with 5% aqueous hydrochloric solution. The solution was extracted with diethyl ether (4×200 mL). All etheral layers were combined, washed with water (100 mL), dried over anhydrous magnesium sulphate and concentrated to give the crude product. GLC analysis showed the following composition: 2-indanone (26.4%), 2-phenyl-indan-2-ol (13.6%), 2-phenyl-1H-indene (11.6%), 1-(2'-indanyl)-2-indanone (48.4%).

EXAMPLE 3 (comparison)

BIS(2-METHYL-INDENYL)ZIRCONIUM DICHLORIDE (a) Preparation of 2-methyl-2-indanol A solution of 36 g of 2-indanone (distilled before use) in 400 ml of anhydrous Et$_2$O was slowly added to a mixture of methyl magnesium bromide (100 ml of a 3M solution in hexane) in 200 ml of Et$_2$O at 0° C. The mixture was added at room temperature. After 3 hours the reaction was stopped with 350 g of ice and a solution of 30 g of NH$_4$Cl in 500 ml of water. The organic layer was separated, washed with 500 ml of a saturated solution of NaHCO$_3$ and then 500 ml of water, dried on sodium sulphate and concentrated under vacuum. 37,8 g of a clear yellow solid was obtained identified as 2-methyl-2-indanol by N.M.R. and GC-MS analysis.

(b) Preparation of 2-methyl-indene 1 g of p-toluene-sulphonic acid monohydrate and 25 g of the product obtained at point (a) were dissolved in 100 ml of toluene. The solution obtained was maintained under reflux for 2 hours. GC analysis of the reaction crude indicated at which point the conversion to 2-methyl-indene was at 96%. The solution was concentrated under vacuum and then distilled in the presence of a small amount of 4-t-butyl-catechol and 2 drops of NaOH. 16.7 g of 2-methyl-indene was obtained having bp. of 58–60° C. at 2 mm Hg.

(c) Preparation of bis(2-methyl-indenyl)zirconium dichloride 4,4 ml of a solution 2.5M of n-butyllithium in hexane were added to a solution of 1.42 g of 2-methyl-indene obtained at point (b), dissolved in 30 ml of THF at 0° C. After the addition the solution was left to return to room temperature and maintained under stirring for a further 4 hours. the volatile substances were removed under vacuum and the solid so obtained was washed with pentane. 1.27 g of $ZrCl_4$ in powder form was added to this solid and the whole was suspended in pentane. In order to facilitate the reaction, 1 ml of THF was added. The suspension was maintained under agitation overnight and at the end the solid was separated by filtration and washed with pentane. The product so obtained was dissolved in $CH_2Cl_2$, filtered, and the solution dried. 1,51 g of a yellow powder was so obtained identified as bis(2-methyl-indenyl)zirconium dichloride from N.M.R. spectra.

EXAMPLE 4

BIS[2-(4-METHYL-PHENYL)-INDENYL] ZIRCONIUM DICHLORIDE (a) Preparation of 2-(p-tolyl)-2-indanol A suspension of anhydrous cerium chloride (40.60 g, 164.7 mmol) in THF(250 mL) was stirred at room temperature for 2 hours under nitrogen. p-Tolylmagnesium bromide (100.0 mL of 1.0 M solution in diethyl ether, 100.0 mmol) was added at 0° C. and stirred for 3.5 h. A solution of 2-indanone (14.21 g, 107.7 mmol) in THF (20 mL) was added at the same temperature. After stirring at 0° C. for 3 h, the mixture was allowed to warm to room temperature and kept at ambient temperature overnight (12 h). It was then treated with 5% aqueous hydrochloric solution. The solution was extracted with diethyl ether (4*200 mL). All etheral layers were combined, washed with water (100 mL), dried over anhydrous magnesium sulphate and concentrated to give the crude product. Kugelrohr distillation yielded 2.94 g of 2-indanone (110° C./0.3 mm Hg) and 17.27 g of 2-(p-tolyl)-2-indanol (160° C./0.3 mm Hg) in solid form. $^1$H-N.M.R. ($CDCl_3$) d 2.17 (br s, 1H), d 2.35 (s, 3H), d 3.22 (d, J=16.2 Hz, 2H), d 3.50 (d, J=16.2 Hz, 2H), d 7.15–7.30 (m, 6H), d 7.45(br d, J=7.1 Hz, 2H).

(b) Preparation of 2-(p-tolyl)-1H-indene

To a solution of 2-(p-tolyl)-2-indanol (17.27 g, 77.01 mmol) in THF (200 mL) was added a solution of concentrated hydrochloric acid (40 mL) in water (60 mL). The solution was stirred at room temperature overnight (12 h). The solid was collected and washed with pentane (50 mL) and then tetrahydrofuran (50 mL) to give 14.77 g of 2-(p-tolyl)-1H-indene. $^1$H-N.M.R. ($CDCl_3$) d 2.43(s, 3H), d 3.83 (br s, 2H), d 7.20–7.35(m, 5H), d 7.45(br d, J=7.1 Hz, 2H), d 7.55(br d, J=7.1 Hz, 2H), d 7.60 (br d, J=7.1 Hz, 2H).

(c) Preparation of bis[2-(4-methyl-phenyl)indenyl] zirconium dichloride 2.4 g of 2-(p-tolyl)-2-indene were suspended in 15 mL THF and added dropwise to 0.52 g of KH in 65 mL THF. At the end of the addition the suspension is stirred for 2 hours at room temperature. Excess KH is decanted off and the yellow-green solution is added dropwise to a solution of 2.2 g of $ZrCl_4(THF)_2$ in 35 mL THF. After the addition is complete, the lemon-yellow suspension is stirred for additional 2 hours, then concentrated in vacuo to a volume of approximately 10 mL, and an equal volume of $Et_2O$ is added. The slurry is stirred for a few minutes, then filtered, washed with $Et_2O$ (2×20 mL) and the solid extracted in a Sohxlet apparatus with $CH_2Cl_2$. After removing $CH_2Cl_2$ in vacuo, a yellow-orange solid (3.31 g) is obtained, which contained 44% of unreacted ligand. 0.65 g of this solid were dissolved in 25 mL toluene and then cooled to −20° C. overnight. 0.332 g of orange needles was obtained. This product was (2-p-Tol-Ind)$_2$ZrCl$_2$ with a purity of 90.4% by weight by N.M.R., the rest being toluene (5.4%) and free ligand (4.2%). Estimated yield 77%. $^1$H-N.M.R. (δ, ppm, $CDCl_3$): 7.44–7.08 (m, 16H), 6.57 (bs, 4H), 2.45 (s, 6H).

EXAMPLE 5

BIS[2-(4-t-BUTYL-PHENYL)-INDENYL] ZIRCONIUM DICHLORIDE (a) Preparation of 2-(4-t-butyl-phenyl)-2-indanol A suspension of anhydrous cerium chloride (40.60 g, 164.7 mmol) in THF(250 mL) was stirred at room temperature for 2 hours under nitrogen. 4-t-Butylphenylmagnesium bromide (70.0 mL of 2.0 M solution in diethyl ether, 140.0 mmol) was added at 0° C. and stirred for 3.5 h. A solution of 2-indanone (14.21 g, 107.7 mmol) in THF (20 mL) was added at the same temperature. After stirring at 0° C. for 3 h, the mixture was allowed to warm to room temperature and kept at ambient temperature overnight (12 h). It was then treated with 5% aqueous hydrochloric solution. The solution was extracted with diethyl ether (4*200 mL). All etheral layers were combined, washed with water (100 mL), dried over anhydrous magnesium sulphate and concentrated to give the crude product. 2-Indanone (1.34 g) was distilled off at 80° C./0.3 mm Hg. The residue was washed with pentane (50 mL) and subject to Kugelrohr distillation(185° C./0.3 mm Hg). 2-(4-t-Butyl-phenyl)-2-indanol (23.43 g) was obtained in pure form. $^1$H-N.M.R. ($CDCl_3$) d 1.32 (s, 9H), d 1.36 (s, 1H), d 3.25 (d, J=16.2 Hz, 2H), d 3.50 (d, J=16.2 Hz, 2H), d 7.15–7.45 (m, 8H)

(b) Preparation of 2-(4-t-butyl-phenyl)-1H-indene

To a solution of 2-(4-t-butyl-phenyl)-2-indanol (23.0 g, 86.5 mmol) in THF (200 mL) was added a solution of concentrated hydrochloric acid (40 mL) in water (60 mL). The solid was collected and washed with pentane (50 mL) and then tetrahydrofuran (50 mL) to give 13.6 g of 2-(4-t-butyl-phenyl)-1H-indene. $^1$H-N.M.R. ($CDCl_3$) d 1.35 (s, 9H), d 3.78(br s, 2H), d 7.13–7.19(m, 2H),d 7.26 (br tt, J=7.4, 0.6 Hz, 1H), d 7.36–7.47(m, 4H), d 7.55–7.6(br d, J=6.7 Hz, 2H).

(c) Preparation of bis[2-(4-t-butyl-phenyl)indenyl] zirconium dichloride 2.5 g of 2-(4-t-butyl-phenyl)-1H-indene were suspended in 40 mL THF and added dropwise to 0.45 g of KH in 60 mL THF. At the end of the addition the suspension is stirred for 2 hours at room temperature. Excess KH is decanted off and the yellow-brown solution is added dropwise to a solution of 1.88 g of $ZrCl_4(THF)_2$ in 20 mL THF. After the addition is complete, the yellow suspension is stirred for additional 18 hours, then concentrated in vacuo to a volume of approximately 20 mL, and an equal volume of $Et_2O$ is added, but no product precipitates. The solution is dried in vacuo obtaining a solid. This yellow solid was extracted with $CH_2Cl_2$, then dried in vacuo, washed with hexane and dried again. yield 2.57 g. This product still contained 19% by weight of free ligand. 1 g of the solid was dissolved in toluene, the solution cooled to −20° C. for three days. 0.3 g of yellow needle-like crystalline [2-(para-tert-butylphenyl)-indenyl]$_2$ZrCl$_2$ was obtained, which had a purity of 93% by weight ($^1$H-N.M.R.), the rest being free ligand (17735/39A). Yield 63%. This product was used without further purification. $^1$H-N.M.R. (δ, ppm, $CDCl_3$): 7.52–7.03 (m, 16H), 6.67 (bs, 4H), 1.42 (s, 18H).

EXAMPLE 6

BIS[2-(4-PHENYL-PHENYL)-INDENYL] ZIRCONIUM DICHLORIDE (a) Preparation of 2-biphenyl-2-indanol A suspension of anhydrous cerium chloride (40.60 g, 164.7 mmol) in THF (250 mL) was stirred at room temperature for 2 hours under nitrogen. A solution of biphenylmagnesium bromide (178 mmol, prepared from magnesium (4.33 g, 178 mmol) and 4-bromobiphenyl (41.50 g, 178 mmol) in ether (60 mL) was added at 0° C. and stirred for 3.5 h. A solution of 2-indanone (14.21 g, 107.7 mmol) in THF (20 mL) was added at the same temperature. After stirring at 0° C. for 3 h, the mixture was allowed to warm to room temperature and kept at ambient temperature for 12 h. It was then treated with 5% aqueous hydrochloric solution. The solution was extracted with diethyl ether (4*200 mL). All etheral layers were combined, washed with water (100 mL), dried over anhydrous magnesium sulphate and concentrated to give the crude product. 2-Indanone and biphenyl were distilled out at 110° C. The residue was washed with pentane (50 mL) to yield 21.65 g of 2-biphenyl-2-indanol in solid form. $^1$H-N.M.R. ($CDCl_3$) d 2.18 (br s, 1H), d 3.27 (d, J=16.2 Hz, 2H), d 3.55 (d, J=16.2 Hz, 2H), d 7.18–7.65 (m, 13H)

(b) preparation of 2-phenyl-1H-indene

To a solution of 2-biphenyl-2-indanol (21.0 g, 73.4 mmol) in THF (200 mL) was added a solution of concentrated hydrochloric acid (40 mL) in water (60 mL). The solution was stirred at room temperature for 3 days. The solid was collected and washed with pentane (50 mL) and then tetrahydrofuran (50 mL) to give 15.1 g of 2-(biphenyl)-1H-indene. $^1$H-N.M.R. ($CDCl_3$) d 3.84 (s, 2H), d 7.20(td, J=7.4, 1.3 Hz, 1H), d 7.26–7.51 (ma, 7H), d 7.61–7.65 (m, 4H), d 7.72 (dt, J=8.1, 2.2 Hz, 2H).

(c) Preparation of bis[2-(4-phenyl-phenyl)indenyl] zirconium dichloride 2.2 g of 2-phenyl-1H-indene were suspended in 20 mL THF and added dropwise to 0.37 g of KH in 50 mL THF. At the end of the addition the suspension is stirred for 2 hours at room temperature. Excess KH is decanted off and the orange solution is added dropwise to a solution of 1.55 g of $ZrCl_4(THF)_2$ in 20 mL THF. After the addition is complete, the arancio suspension is stirred for additional 18 hours, then concentrated in vacuo to a volume of approximately 10 mL, and an equal volume of $Et_2O$ is added. The slurry is stirred for a few minutes, then filtered, and the solid washed with $CH_2Cl_2$, which does not dissolve the zirconocene. The yellow solid is then dried in vacuo, yield 2.08 g. This product still contained 19% by weight of free ligand. This was washed with 5 mL HCl 4N, 5 mL $H_2O$, 5 mL EtOH and 2×5 mL $Et_2O$, dried in vacuo. Yield 1.53 g of a product which still contained 10% weight of free ligand (yield 53%). This product was used without further purification. $^1$H-N.M.R. (δ, ppm, $CDCl_3$): 7.66–7.10 (m, 26H), 6.75 (bs, 4H).

EXAMPLE 7

BIS[2- (4-FLUORO-PHENYL)-INDENYL] ZIRCONIUM DICHLORIDE (a) preparation of 2-(4-fluorophenyl)-2-indanol A suspension of anhydrous cerium chloride (43.9 g, 178.0 mmol) in THF (250 mL) was stirred at room temperature for 2 hours under nitrogen. 4-Fluorophenylmagnesium bromide (75.6 mL of 2.0 M solution in diethyl ether, 151.2 mmol) was added at 0° C. and stirred for 3.5 h. A solution of 2-indanone (15.36 g, 116.4 mmol) in THF (20 mL) was added at the same temperature. After stirring at 0° C. for 3 h, the mixture was allowed to warm to room temperature and kept at ambient temperature over-night (12 h). It was then treated with 5% aqueous hydrochloric solution. The solution was extracted with diethyl ether (4*200 mL). All etheral layers were combined, washed with water (100 mL), dried over anhydrous magnesium sulphate and concentrated to give the crude product. Unreacted 2-indanone was distilled off. The residue was subjected to Kugelrohr distillation (165° C./0.3 mm Hg). 2-(4-Fluorophenyl)-2-indanol (21.62 g) was obtained in pure form. $^1$H-N.M.R. ($CDCl_3$) d 2.22 (br s, 1H), d 3.24 (d, J=16.3 Hz, 2H), d 3.47 (d, J=16.3 Hz, 2H), d 7.04 (m, 2H), d 7.20–7.28(m, 4H), d 7.52(br d, J=9.0, 5.3 Hz, 2H).

(b) preparation of 2-(4-fluorophenyl)-1H-indene

To a solution of 2-(4-fluorophenyl)-2-indanol (21.0 g, 92.1 mmol) in THF (200 mL) was added a solution of concentrated hydrochloric acid (40 mL) in water (60 mL). The solution was stirred at room temperature overnight (14 h). The solid was collected and washed with pentane (50 mL) and then tetrahydrofuran (50 mL) to give 13.7 g of.yield 2-(4-fluorophenyl)-1H-indene. $^1$H-N.M.R. ($CDCl_3$) d 3.78 (br s, 2H), d 7.05 (br d, J=8.6 Hz, 2H), d 7.13(br s, 1H), d 7.17(tt, J=7.4, 1.2 Hz, 1H), d 7.7(br t J=7.4 Hz, 1H), d 7.38(br d, J=7.4Hz, 1H), d 7.45(br d, J=7.4 Hz, 1H), d 7.57(br dd, J=9.0, 5.4 Hz, 2H)

(c) Preparation of bis[2-(4-fluoro-phenyl)indenyl]zirconium dichloride 3.0 g of b were suspended in 25 mL THF and added dropwise to 0.64 g of KH in 90 mL THF. At the end of the addition the suspension is stirred for 2 hours at room temperature. Excess KH is decanted off and the orange solution is added dropwise to a solution of 2.69 g of $ZrCl_4(THF)_2$ in 45 mL THF. After the addition is complete, the yellow-green suspension is stirred for additional 2 hours (the colour turns to yellow), then concentrated in vacuo to a volume of approximately 5 mL, and an equal volume of $Et_2O$ is added. The slurry is stirred for a few minutes, then filtered, and the solid was extracted with $CH_2Cl_2$. The yellow solid is then dried in vacuo, yield 3.4 g. This product still contained 36% by weight of free ligand. 2 g of the solid was dissolved in toluene, the solution cooled to −20° C. for three days. 0.82 g of lemon-yellow [2-(para-fluorophenyl)-indenyl]$_2$ZrCl$_2$ was obtained, which had a purity of 95% by weight ($^1$H-N.M.R.), the rest being toluene (3%) and free ligand (2%). Yield 50%. This product was used without further purification. $^1$H-N.M.R. (δ, ppm, $CDCl_3$): 7.48–7.05 (m, 16H), 6.54 (bs, 4H).

EXAMPLE 8

BIS[2-(3,5-DIMETHYL-PHENYL)-INDENYL] ZIRCONIUM DICHLORIDE (a) Preparation of 2-(3,5-xylenyl)-2-indanol A suspension of anhydrous cerium chloride (43.88 g, 178.1 mmol) in THF (250 mL) was stirred at room temperature for 2 hours under nitrogen. A solution of 3,5-m-xylenylmagnesium bromide (178 mmol, prepared from magnesium (4.33 g, 178.1 mmol) and 5-bromo-m-xylene (24.2 mL, 178.1 mmol) in ether (60 mL) was added at 0° C. and stirred for 3.5 h. A solution of 2-indanone (14.21 g, 107.7 mmol) in THF (20 mL) was added at the same temperature. After stirring at 0° C. for 3 h, the mixture was allowed to warm to room temperature and kept at ambient temperature for 12 h. It was then treated with 5% aqueous hydrochloric solution. The solution was extracted with diethyl ether (4*200 mL). All etheral layers were combined, washed with water (100 mL), dried over anhydrous magnesium sulphate and concentrated to give the crude product. 2-Indanone was distilled out at 80° C. (0.3 mm Hg). The residue was washed with pentane (50 mL) to yield 21.57 g of 2-(3,5-xylenyl)-2-indanol in solid form.

(b) preparation of 2-(3,5-xylenyl)-1H-indene

To a solution of 2-biphenyl-2-indanol (21.0 g, 73.4 mmol) in THF (200 mL) was added a solution of concentrated hydrochloric acid (40 mL) in water (60 mL). The solution was stirred at room temperature for 3 days. The solid was collected and washed with pentane (50 mL) and then tetrahydrofuran (50 mL) to give 15.75 g of 2-(3,5-xylenyl)-1H-indene.

(c) Preparation of bis[2-(3,5-dimethyl-phenyl)indenyl] zirconium dichloride 3.0 g of b (81% weight, the rest being the coupling product) were dissolved in 40 mL THF and added dropwise to 0.49 g of KH in 50 mL THF. At the end of the addition the suspension is stirred for 2 hours at room temperature. Excess KH is decanted off and the brown solution is added dropwise to a solution of 2.08 g of $ZrCl_4(THF)_2$ in 30 mL THF. After the addition is complete, the brown suspension is stirred for additional 18 hours, then concentrated in vacuo to a volume of approximately 20 mL, and an equal volume of $Et_2O$ is added. The slurry is stirred for a few minutes, then filtered, washed with $Et_2O$ (2×20 mL) and the solid extracted in a Sohxlet apparatus with $CH_2Cl_2$. After removing $CH_2Cl_2$ in vacuo, a yellow sticky solid is obtained, which was washed with $Et_2O$ and dried -in vacuo, yield 2.3 g. This product was bis[2-(3,5-dimethyl-phenyl)indenyl] zirconium dichloride with a purity of 95.3% by weight by N.M.R., the rest being free ligand. Estimated yield 66%. $^1$H-N.M.R. (δ, ppm, $CDCl_3$): 7.17–7.08 (m, 14H), 6.53 (bs, 4H), 2.42 (s, 12H).

EXAMPLE 9

BIS[2-(2-METHYL-PHENYL)-INDENYL] ZIRCONIUM DICHLORIDE (a) preparation of 2-(o-tolyl)-2-indanol A suspension of anhydrous cerium chloride (40.60 g, 164.7 mmol) in THF(250 mL) was stirred at room temperature for 2 hours under nitrogen. o-Tolylmagnesium bromide (70.0 mL of 2.0 M solution in diethyl ether, 140.0 mmol) was added at 0° C. and stirred for 3.5 h. A solution of 2-indanone (14.21 g, 107.7 mmol) in THF (20 mL) was added at the same temperature. After stirring at 0° C. for 3 h, the mixture was allowed to warm to room temperature and kept at ambient temperature overnight (12 h). It was then treated with 5% aqueous hydrochloric solution. The solution was extracted with diethyl ether (4*200 mL). All etheral layers were combined, washed with water (100 mL), dried over anhydrous magnesium sulphate and concentrated to give the crude product. Kugelrohr distillation (120° C./0.3 mm Hg) yielded 4.0 g of 2-indanone and 10.38 g of 2-(o-tolyl)-2-indanol in solid form. $^1$H-N.M.R. ($CDCl_3$) d 2.13 (br s, 1H), d 2.52(s, 3H), d 3.36 (d, J=16.2 Hz, 2H), d 3.63 (d, J=16.2 Hz, 2H), d 7.15–7.62 (m, 8H)

(b) preparation of 2-(o-tolyl)-1H-indene

To a solution of 2-(o-tolyl)-2-indanol (10.0 g, 44.6 mmol) in THF (200 mL) was added a solution of concentrated hydrochloric acid (40 mL) in water (60 mL). The solution was stirred at room temperature overnight (12 h). Diethyl ether (200 mL) and water added. Aqueous layer was extracted with diethyl ether (3*200 mL). All etheral layers were combined, washed with water (50 mL), brine (50 mL), dried over anhydrous magnesium sulphate, and concentrated. Kugelrohr distillation yielded 5.8 g of 2-(o-tolyl)-1H-indene (150° C./0.3 mm Hg). $^1$H-N.M.R. ($CDCl_3$) d 2.49(s, 3H), d 3.78 (d, J=0.90 Hz, 2H), d 6.94(br s, 1H), d 7.18–7.50(m, 8H).

(c) Preparation of bis[2-(2-methyl-phenyl)indenyl] zirconium dichloride 2.606 g of 2b were dissolved in 40 mL THF and added dropwise to 0.564 g of KH in 50 mL THF. At the end of the addition the suspension is stirred for 2 hours at room temperature. Excess KH is decanted off and the yellow-green solution is added dropwise to a solution of 2.39 g of $ZrCl_4(THF)_2$ in 20 mL THF. After the addition is complete, the brown-yellow suspension is stirred for additional 20 hours, then concentrated in vacuo to a volume of approximately 20 mL, and an equal volume of $Et_2O$ is added. The slurry is stirred for a few minutes, then filtered, washed with $Et_2O$ (2×20 mL) and the solid extracted in a Sohxlet apparatus with $CH_2Cl_2$. After removing $CH_2Cl_2$ in vacuo, a yellow sticky solid (1.64 g) is obtained, which was then treated with 40 mL toluene, filtered and the filtrate cooled to −20° C. 0.1 g of yellow microcrystalline product was obtained. The solid residue was dried in vacuo (0.65 g). Both fractions were (2-o-Tol-Ind)$_2$ZrCl$_2$ with the same purity (97% by weight) by N.M.R. Combined yield 21%. $^1$H-N.M.R. (δ, ppm, $CDCl_3$): 7.51–7.18 (m, 16H), 6.31 (bs, 4H), 2.45 (s, 6H).

POLYMERIZATION OF PROPYLENE
METHYLALUMOXANE (MAO)

A commercial (Schering, MW 1400) 30% toluene solution of MAO was used. After having removed the volatile fractions under vacuum, a solid glassy material was finely crushed and further treated in vacuo (0.1 mmHg) for 4–6 hours, at a temperature of 40–50° C. to leave a white, free-flowing powder.

MODIFIED METHYLALUMOXANE (M-MAO)

A commercial product (Ethyl) has been used as received in solution (62 g Al/l) in isopar C.

EXAMPLES 10–17

Into a 1 litre autoclave, equipped with a jacket, stirrer and thermoresistance, and connected to a thermostat for temperature control, dried at 80° C. in a propylene flow, 220 g of propylene were charged and the temperature was brought up to the value indicated in Table 1. Then a toluene solution containing bis(2-phenyl-indenyl)zirconium dichloride prepared as described in Example 1 and MAO or M-MAO in the amounts indicated in Table 1 was injected into the autoclave through a steel ampulla. After 1 hour of reaction, the non reacted monomers were degassed and the product obtained was dried. The polymerization conditions and the data relating to the characterisation of the polymer produced are reported in Table 1. The polymer obtained in Example 14 was fractionated in Kumagawa with diethyl ether for 14 hours, then with n-hexane for 24 hours, then with n-heptane for 15 hours. The n-heptaneinsoluble fraction was dissolved in xylene at 135° C. The characterization data of the obtained fractions are reported in Table 2.

EXAMPLE 18 (comparison)

It was worked according to the process described in examples 10–17, but using bis(2-methyl-indenyl)zirconium dichloride instead of bis(2-phenyl-indenyl)zirconium dichloride. The polymerization conditions and the data relating to the characterisation of the polymer produced are reported in Table 1. From DSC analysis no peak was observed attributable to the enthalpy of fusion.

EXAMPLES 19–27

It was worked according to the process described in examples 10–17, but using the metallocene indicated in Table 1 instead of bis(2-phenyl-indenyl)zirconium dichloride. The polymerization conditions and the data relating to the characterisation of the polymer produced are reported in Table 1.

EXAMPLE 28 (comparison)

It was worked according to the process described in examples 10–17, but using bis[2-(2-methyl-phenyl)indenyl] zirconium dichloride instead of bis(2-phenyl-indenyl) zirconium dichloride. The polymerization conditions are reported in Table 1. No polymer was obtained.

What is claimed is:

1. A process for the preparation of a propylene polymer, the propylene polymer being a fractionable propylene polymer, directly obtainable from the polymerization reaction of propylene, having the following characteristics:
    (a) content of isotactic pentads (mmmm) comprised between 25% and 85%;
    (b) ratio $M_w/M_n$, <5;
    said polymer containing from 10% to 70% by weight based on the total weight of said polymer of a fraction soluble in boiling diethylether, said fraction having a content of isotactic pentads (mmmm) com-

TABLE 1

| EXAMPLE | metallocene | cocat. | Zr (μmoles) | Al/Zr (mol) | solution (mL) | T (° C.) | yield (grams) | activity ($Kg_{pol}$/mmol$_z$h) |
|---|---|---|---|---|---|---|---|---|
| 10(a) | (2-Ph—Ind)$_2$ZrCl$_2$ | MAO | 13.2 | 1100 | 16.5 | 5 | 18.8 | 0.7 |
| 11(b) | " | MAO | 13.2 | 1100 | 25.0 | 20 | 46.8 | 1.7 |
| 12 | " | MAO | 3.7 | 1500 | 4.0 | 20 | 4.2 | 1.1 |
| 13(b)(c) | " | MAO | 13.2 | 1100 | 25.0 | 30 | 9.8 | 0.3 |
| 14 | " | M-MAO | 3.7 | 3000 | 7.0 | 40 | 7.3 | 2.0 |
| 15 | " | MAO | 1.8 | 3000 | 4.0 | 50 | 3.7 | 2.0 |
| 16 | " | M-MAO | 1.8 | 3000 | 3.4 | 50 | 5.8 | 3.1 |
| 17 | " | M-MAO | 11.0 | 500 | 8.4 | 50 | 27.7 | 2.5 |
| 18(COMP)(a) | (2-Me—Ind)$_2$ZrCl$_2$ | M-MAO | 8.8 | 1000 | 16.5 | 50 | 57 | 6.5 |
| 19 | [2(4-Me—Ph)—Ind]$_2$ZrCl$_2$ | MAO | 5.2 | 1000 | 5.1 | 50 | 7.1 | 1.3 |
| 20 | " | M-MAO | 5.5 | 500 | 8.7 | 50 | 15.07 | 1.4 |
| 21 | [2(4-t-Bu—Ph)—Ind]$_2$ZrCl$_2$ | M-MAO | 5.5 | 500 | 6.0 | 50 | 11.2 | 1.0 |
| 22 | [2(4-Ph—Ph)—Ind]$_2$ZrCl$_2$ | M-MAO | 1.4 | 3000 | 4.9 | 50 | 3.2 | 2.2 |
| 23 | " | M-MAO | 11.0 | 500 | 6.3 | 50 | 25.0 | 2.3 |
| 24 | [2(4-Ph—Ph)—Ind]$_2$ZrCl$_2$ | M-MAO | 11.0 | 3000 | 18.0 | 50 | 27.5 | 2.5 |
| 25 | [2(4-F—Ph)—Ind]$_2$ZrCl$_2$ | M-MAO | 1.7 | 3000 | 3.7 | 50 | 3.1 | 1.8 |
| 26 | " | M-MAO | 11.0 | 500 | 8.8 | 50 | 22.6 | 2.0 |
| 27 | [2(3,5-Me$_2$—Ph)—Ind]$_2$ZrCl$_2$ | M-MAO | 1.7 | 3000 | 5.0 | 50 | 1.1 | 0.7 |
| 28(COMP) | [2(2-Me—Ph)—Ind]$_2$ZrCl$_2$ | M-MAO | 1.7 | 3000 | 4.3 | 50 | 0 | 0 |

| EXAMPLE | I.V. (dL/g) | $T_m$ (° C.) | $\Delta H_f$ (J/g) | $M_w/M_n$ | mmmm (%) | m-r (%) | B |
|---|---|---|---|---|---|---|---|
| 10(a) | 4.61 | 144.8 | 10.9 | | 24.1 | 29.41 | 1.57 |
| 11(b) | 2.87 | 148.1 | 26.5 | 3.2 | 38.6 | 46.15 | 2.56 |
| 12 | 2.97 | 145.8 | 26.9 | | 33.5 | 41.07 | 1.93 |
| 13(b)(c) | 1.93 | 147.4 | 22.1 | | 38.3 | 45.56 | 2.33 |
| 14 | 0.91 | | | | 30.6 | 38.10 | 2.01 |
| 15 | 0.70 | | | | 23.8 | 28.46 | 1.68 |
| 16 | 0.50 | | | | | | |
| 17 | 0.56 | | | | | | |
| 18(COMP)(a) | 0.26 | | 0 | | 8.3 | 7.72 | 0.98 |
| 19 | 0.82 | | | | | | |
| 20 | 0.60 | | | | 28.1 | 33.94 | 1.91 |
| 21 | 0.50 | | | | 20.2 | 24.76 | 1.62 |
| 22 | 0.99 | | | | 32.2 | 37.18 | 2.37 |
| 23 | 0.65 | | | | 34.7 | 39.91 | 2.45 |
| 24 | 0.54 | | | | | | |
| 25 | 0.72 | | | | | | |
| 26 | 0.51 | | | | 19.0 | 22.60 | 1.49 |
| 27 | 0.39 | | | | 25.3 | 32.64 | 1.55 |
| 28(COMP) | | | | | | | |

(a) 1.35 liter autoclave, 550 g of propilene
(b) 4.25 liter autoclave, 1600 g of propilene
(c) catalyst precontacted 20 minutes

TABLE 2

| FRACTION | soluble (% weight) | $T_m$ (° C.) | $\Delta H$ (J/g) | I.V. (dL/g) | $M_w/M_n$ | mmmm (%) | m-r (%) | B |
|---|---|---|---|---|---|---|---|---|
| Example 11 | — | 148.1 | 26.5 | 2.9 | 3.2 | 38.6 | 46.15 | 2.56 |
| Et$_2$O soluble | 35 | amorphous | — | 2.1 | 3.0 | 17.3 | 22.93 | 1.22 |
| hexane soluble | 11 | broad peak | — | 2.0 | 2.7 | 37.5 | 45.16 | 2.29 |
| heptane soluble | 7 | 141 | 3.3 | 2.7 | 2.6 | 51.0 | 61.69 | 2.93 |
| xylene soluble | 47 | 145 | 51.3 | 4.1 | 3.0 | 66.3 | 73.01 | 6.09 | prised between 5% and 25%, and from 30% to 90% by weight based on the total weight of said polymer of a boiling-heptane-insoluble fraction, which is soluble in xylene at 135° C., said fraction having a content of isotactic pentads (mmmm) comprised between 50% and 99%;

the process comprising comprising the polymerization reaction of propylene, in a polymerization medium consisting essentially of liquid propylene, in the presence of a catalyst comprising the product of the reaction between:

(A) a metallocene compound of formula (1):

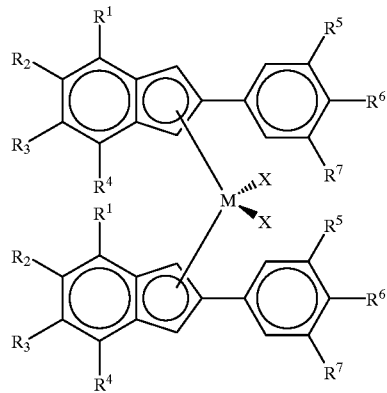

(I)

wherein on each indenyl group the $R^1$, $R^2$, $R^3$, $R^4$, $R^5$, $R^6$, and $R^7$ substituents, same or different from each other, are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$-aryl radicals, $C_7$–$C_{20}$ alkylaryl radicals, or $C_7$–$C_{20}$ arylalkyl radicals, optionally two adjacent $R^1$, $R^2$, $R^3$, $R^4$, $R^5$, $R^6$, and $R^7$ substituents on the same ring can form a cycle comprising 5 to 8 carbon atoms and, furthermore, substituents $R^1$ can contain Si or Ge atoms;

M is a transition metal of group IVb, Vb, or VIb of the Periodic Table of the Elements;

substituents X, the same or different from each other, are hydrogen atoms, halogen atoms, —$R^8$, —$OR^8$, —$SR^8$, $NR^8{}_2$, or —$PR^8{}_2$ groups, wherein substituents $R^8$ are $C_1$–$C_{20}$ alkyl radicals, $C_3$–$C_{20}$ cycloalkyl radicals, $C_2$–$C_{20}$ alkenyl radicals, $C_6$–$C_{20}$-aryl radicals, $C_7$–$C_{20}$ alkylaryl radicals, or $C_7$–$C_{20}$ arylalkyl radicals, and can contain Si or Ge atoms; and (B) an alumoxane, or one or more compounds able to give a metallocene alkyl cation.

2. The process according to claim 1, wherein the polymerization temperature is comprised between 20° C. and 40° C.

3. The process according to claim 1 wherein, in the metallocene compound of formula (I), all the substituents $R^1$, $R^2$, $R^3$ and $R^4$ are hydrogen atoms.

4. The process according to claim 1 wherein, in the metallocene compound of formula (I), the transition metal M is selected among titanium, zirconium and hafnium.

5. The process according to claim 1 wherein, in the metallocene compound of formula (I), the substituents X are chlorine atoms or methyl radicals.

6. The process according to claim 1, wherein the alumoxane is methylalumoxane.

7. The process according to claim 4 wherein the transition metal is zirconium.

* * * * *

UNITED STATES PATENT AND TRADEMARK OFFICE
CERTIFICATE OF CORRECTION

PATENT NO. : 6,107,431 Page 1 of 1
DATED : August 22, 2000
INVENTOR(S) : Luigi Resconi et al.

It is certified that error appears in the above-identified patent and that said Letters Patent is hereby corrected as shown below:

Column 18, claim 1,
Line 8, please change "$M_w/M_n,<5$" to -- $M_w/M_n<5$ --

Column 19, claim 1,
Line 7, delete the second occurrence of "comprising"

Signed and Sealed this

Eighth Day of January, 2002

Attest:

Attesting Officer

JAMES E. ROGAN
Director of the United States Patent and Trademark Office